United States Patent [19]
Hasenoehrl et al.

[11] Patent Number: 6,093,408
[45] Date of Patent: *Jul. 25, 2000

[54] SKIN CARE COMPOSITIONS

[75] Inventors: Erik John Hasenoehrl, Hyde Park; Jeanne Marie Ponte, Loveland, both of Ohio; Anthony Daniel Sabatelli, Wilder, Ky.

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/736,688

[22] Filed: Oct. 25, 1996

Related U.S. Application Data

[60] Provisional application No. 60/007,254, Nov. 6, 1995, abandoned.

[51] Int. Cl.$^7$ .................................................. A61K 7/48
[52] U.S. Cl. ..................... 424/401; 514/159; 514/292; 514/345; 514/354; 514/357; 514/456; 514/563; 514/685; 514/783; 514/845; 514/846; 514/859; 514/937
[58] Field of Search ................. 424/401; 514/844, 514/845, 846, 859, 937, 159, 292, 345, 354, 357, 563, 456, 685, 783

[56] References Cited

U.S. PATENT DOCUMENTS

| | | | |
|---|---|---|---|
| 4,515,784 | 5/1985 | Bogardus et al. | 514/63 |
| 5,036,108 | 7/1991 | Asahi et al. | 514/772 |
| 5,066,485 | 11/1991 | Brieva et al. | 424/63 |
| 5,073,371 | 12/1991 | Turner et al. | 424/401 |
| 5,073,372 | 12/1991 | Turner et al. | 424/401 |
| 5,118,507 | 6/1992 | Clement | 424/401 |
| 5,302,382 | 4/1994 | Kasprzak | 424/78.03 |
| 5,380,528 | 1/1995 | Alban et al. | 424/401 |
| 5,420,118 | 5/1995 | Alban et al. | 514/63 |
| 5,443,760 | 8/1995 | Kasprzak | 424/78.03 |
| 5,607,980 | 3/1997 | McAtee et al. | 514/476 |
| 5,665,364 | 9/1997 | McAtee et al. | 424/401 |

FOREIGN PATENT DOCUMENTS

| | | |
|---|---|---|
| 0 279 319 | 8/1988 | European Pat. Off. . |
| 0 373 661 | 6/1990 | European Pat. Off. . |
| 0 627 215 A1 | 12/1994 | European Pat. Off. . |
| 0 627 259 A2 | 12/1994 | European Pat. Off. . |
| 0 638 308 A1 | 2/1995 | European Pat. Off. . |
| 2 230 186 | 10/1990 | United Kingdom . |
| 94/02176 | 2/1994 | WIPO . |
| 96/17672 | 6/1996 | WIPO . |
| 97/08053 | 3/1997 | WIPO . |

OTHER PUBLICATIONS

Dow Corning Corporation, 1987, *Information About Cosmetic Ingredients*.

Dow Corning Corporation, 1990, *Dow Corning 4225C Formulation Aid*.

*Primary Examiner*—Jyothsna Venkat
*Attorney, Agent, or Firm*—David L. Suter

[57] ABSTRACT

The present invention provides compositions and methods for treatment of human skin. Such methods include those for regulating sebum on facial skin of a human subject, comprising applying to said subject an emulsion composition comprising (a) an anhydrous silicone mixture comprising
  (i) an ethylene oxide/propylene oxide silicone copolymer;
  (ii) an ethylene oxide silicone copolymer;
  (iii) a silicone gum; and
  (iv) a silicone fluid; and
(b) water.

12 Claims, No Drawings

SKIN CARE COMPOSITIONS

CROSS REFERENCE

This application claims priority under Title 35, United States Code 119(e) from Provisional Application Ser. No. 60/007,254, filed Nov. 6, 1995 now abandoned.

BACKGROUND OF THE INVENTION

The present invention relates to cosmetic compositions and methods. In particular it relates to cosmetic compositions for regulating sebum on the skin. These compositions may also include acne treatment actives.

A wide variety of compositions are known in the art for providing cosmetic and/or pharmacologic benefits to human skin. Benefits sought include, for example, prevention, treatment or amelioration of environmental or age-related damage or deterioration of the skin, improved appearance by modifying surface characteristics, improved feel by moisturizing, and prevention or treatment of specific skin disorders. Many conventional cosmetic cream and lotion compositions as described, for example, in Sagarin, *Cosmetics Science and Technology*, 2nd Edition, Volume 1, Wiley Interscience (1972), and *Encyclopedia of Chemical Technology*, Third Edition, Volume 7. However, because of the physiological complexity of the skin (manifested, for example, by the skin's inherent barrier characteristics to many materials), the ability of such compositions to provide their intended benefits is often limited.

An important aspect of providing cosmetic and/or therapeutic benefits often includes the control of sebum, or skin oil. Sebum is produced in the sebaceous glands located in the pilosebaceous apparatus of the skin and reaches the skin surface through the duct of the hair follicles. The presence of excessive amounts of sebum on the skin surface often results in an unattractive cosmetic condition commonly known as "oily skin". Sebum also plays an important role in the pathogenesis of acne. Acne is a pilosebaceous disease characterized by comedo, papules, inflamed nodules and superficial pus-filled cysts. The course and severity of acne is determined by the interaction between hormones, keratinization, sebum formation and bacteria. Acne usually begins at puberty, when the pilosebaceous glands increase in size, and sebum synthetic activity is elevated due to increased circulating levels of androgens. Follicular hyperkeratosis can also occur, causing restriction of pilosebaceous follicles and, consequently, comedo or plug formation. The comedo contains sebum, protein debris, and anaerobic microorganisms including Propionibacterium (Corynebacterium) acnes. *P. acnes* thrive on sebum and generate inflammatory free fatty acids. These acids cause irritation in the follicular wall and can lead to rupture of the follicular wall, inducing an inflamed lesion. In severe cases, this lesion will heal with scarring.

Thus, control of sebum on the surface of skin can provide important benefits in the treatment or prevention of acne, as well as improving the appearance of skin by reducing perceived oiliness and greasiness. A variety of compositions have been described in the art for the regulation of sebum on the skin. Typically, the problem of oily facial skin has been dealt with by frequent cleansing and the use of astringent preparations. Clays, talcs, silicas, starches, polymers, and other similar materials have been also suggested for use in skin care compositions for absorbing sebum and controlling oily skin. Topical or systemic pharmacologic agents have also been suggested, to inhibit the product production of sebum. See Karg, G. et al., "Sebosuppression", *Cosmetics & Toiletries*, vol. 102, pp. 140–146 (April 1987). Skin care compositions said to affect sebum on the skin are described in U.S. Pat. No. 4,515,784, Bogardus et al., issued May 7, 1985; U.S. Pat. No. 5,073,371, Turner et al., issued Dec. 17, 1991; U.S. Pat. No. 5,073,372, Turner et al., issued Dec. 17, 1991; and U.S. Pat. No. 5,380,528, Alban et al., issued Jan. 10, 1995.

However, many compositions known in the art either provide benefits that are very limited, in terms of degree of efficacy, duration of efficacy, or both. Many such compositions also create undesirable side effects. For example, some compositions may create unacceptable drying, irritation or abrasion of the skin. Others may result in undesirable systemic side effects, such as diuretic activity, inflammation, increased blood pressure and effects on other bodily functions. Furthermore, many products actually contribute to and aggravate oily skin problems. For example, many emulsion products are oil-in-water or water-in-oil emulsions containing high levels of fats and oils. The high levels of fats and oils in these products may, in fact, add to the level of oils on the skin.

Applicants have found that compositions containing certain mixtures of silicone materials, in an emulsion, provide significant benefits for the regulation of sebum on skin. Preferred compositions include sebum controlling materials, or other acne regulating agents. These compositions provide improved cosmetic benefits (such as improvement in the visual appearance and feel of skin), as well as improved application characteristics, compared to compositions amongst those known in the art.

SUMMARY OF THE INVENTION

The present invention provides compositions and methods for treatment of human skin. Such methods include those for regulating sebum on facial skin of a human subject, comprising applying to said subject an emulsion composition comprising
  (a) an anhydrous silicone mixture comprising
    (i) an ethylene oxide/propylene oxide silicone copolymer;
    (ii) an ethylene oxide silicone copolymer;
    (iii) a silicone gum; and
    (iv) a silicone fluid; and
  (b) water.
Preferred emulsion compositions comprise:
  (a) a safe and effective amount of an acne regulating agent;
  (b) an anhydrous silicone mixture comprising
    (i) an ethylene oxide/propylene oxide silicone copolymer;
    (ii) an ethylene oxide silicone copolymer;
    (iii) a silicone gum; and
    (iv) a silicone fluid; and
  (c) water.
Preferably, compositions include an acne regulating agent selected from the group of sebum controlling agents, keratolytic agents, antibacterials, and mixtures thereof Preferred sebum controlling agents include nicotinic acid, niacinamide, cucumber extract, panthenol, pantothenic acid, pyridoxine, riboflavin, retinoids, hesperitin, phloretin, and mixtures thereof

DETAILED DESCRIPTION OF THE INVENTION

The present invention provides compositions and methods for application to human skin, for providing cosmetic and/or therapeutic benefits. Thus, specific compounds and compositions to be used in these compositions and methods must, be cosmetically and/or pharmaceutically-acceptable. As used herein, such a "cosmetically acceptable" or "pharmaceutically-acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired cosmetic benefit or therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular benefit desired, the physical condition of the subject, the duration of the use of the composition, the nature of any concurrent product use (if any), and the specific formulations employed.

Compositions

The compositions of this invention comprise a mixture of silicone materials (herein "anhydrous silicone mixture"). Specifically, the anhydrous silicone mixture comprises:

(i) an ethylene oxide/propylene oxide silicone copolymer;
(ii) an ethylene oxide silicone copolymer;
(iii) a silicone gum; and
(iv) a silicone fluid.

Ethylene oxide/propylene oxide silicone copolymer:

The anhydrous silicone mixtures useful in this invention include a silicone copolymer of the following formula (herein referred to as an "ethylene oxide/propylene oxide silicone copolymer"):

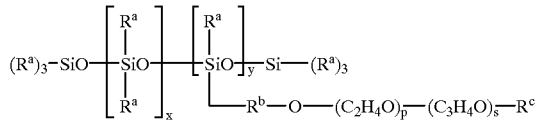

wherein $R^a$ is an alkyl group of one to six carbon atoms; $R^b$ is the radical —$C_mH_{2m}$—; $R^c$ is a terminating radical which can be hydrogen, an alkyl group of one to six carbon atoms, or an aryl group such as phenyl; "m" has a value of two to eight; "p" and "s" have values such that the oxyalkylene segment —$(C_2H_4O)_p$—$(C_3H_6O)_s$— has a molecular weight in the range of 400 to 5,000; the segment preferably having fifty to one hundred mole percent of oxyethylene units —$(C_2H_4O)_p$ and one to fifty mole percent of oxypropylene units —$(C_3H_6O)_p$; "x" has a value of 80 to 120; and "y" has a value of 2 to 10.

Preferably $R^a$ and the terminating radical $R^c$ are methyl groups; "m" is preferably 3 or 4 whereby the group $R^b$ is most preferably the radical —$(CH_2)_3$—; and the values of "p" and "s" are such as to provide a molecular weight of the oxyalkylene segment—$(C_2H_4O)_p$—$(C_3H_6)_s$— of between about 1,000 to 3,000. Most preferably "p" and "s" should each have a value of about 18 to 28.

Ethylene oxide/propylene oxide silicone copolymers useful herein include those described in U.S. Pat. No. 5,302,382, Kasprzak, issued Apr. 12, 1994 (incorporated by reference herein). A preferred ethylene oxide/propylene oxide silicone copolymer is Dow Corning 3225, marketed by Dow Corning Corporation.

Ethylene oxide silicone copolymer:

The anhydrous silicone mixtures useful in this invention include a silicone copolymer of the following formula (herein referred to as an "ethylene oxide silicone copolymer"):

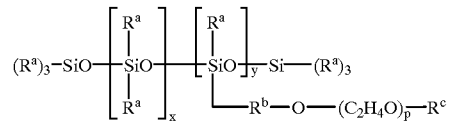

wherein $R^a$ is an alkyl group of one to six carbon atoms; $R^b$ is the radical —$C_mH_{2m}$—; $R_c$ is a terminating radical which can be hydrogen, an alkyl group of one to six carbon atoms, or an aryl group such as phenyl; "m" has a value of two to eight; "p" has a value of 8 to 16; "x" has a value of 6 to 12; and "y" has a value of 1 to 8.

Ethylene oxide silicone copolymers useful herein include those described in U.S. Pat. No. 5,302,382, Kasprzak, issued Apr. 12, 1994 (incorporated by reference herein). A preferred ethylene oxide silicone copolymer is Dow Corning 193, marketed by Dow Corning Corporation.

Silicone gum:

The anhydrous silicone mixtures useful in this invention include a silicone gum having a molecular weight of from about 200,000 to about 600,000. Specific examples include polydimethylsiloxane, (polydimethylsiloxane) (methylvinylsiloxane) copolymer, poly(dimethylsiloxane) (diphenyl) (methylvinylsiloxane) copolymer and mixtures thereof Silicone gums useful herein include silicones having a molecular weight of from about 200,000 to about 540,000 selected from the group consisting of dimethiconol, fluorosilicone and dimethicones or mixtures thereof Dimethiconols useful herein include those with the following chemical structure

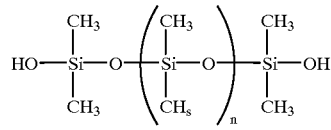

wherein "n" is from about 2700 to about 4500, preferably from about 3200 to about 4300, more preferably from about 4000 to about 4300. The dimethiconol component has a molecular weight of from about 200,000 to about 300,000, preferably from about 240,000 to about 260,000, more preferably about 250,000. The fluorosilicones useful in the present invention have a molecular weight of from about 200,000 to about 300,000, preferably from about 240,000 to about 260,000, more preferably about 250,000.

Dimethicones amongst those useful herein are described in the following publications incorporated by reference herein: U.S. Pat. No. 4,152,416, Spitzer et al., issued May 1, 1979; and Noll, Walter, *Chemistry and Technology of Silicones*, New York: Academic Press (1968). Also describing silicone gums are General Electric Silicone Rubber Product Data Sheets SE 30, SE 33, SE 54 and SE 76. A preferred silicone gum useful herein is Dow Corning 1401, marketed by the Dow Corning Corporation.

Silicone Fluid:

The anhydrous silicone mixtures useful in this invention include a silicone fluid. The silicone fluid may be either a polyalkyl siloxane, a polyaryl siloxane, a polyalkylaryl siloxane or a polyether siloxane copolymer. Mixtures of these fluids may also be used.

The polyalkyl siloxane fluids that may be used include, for example, polydimethyl siloxanes with viscosities ranging from about 5 to about 600,000 centistokes at 25° C. These siloxanes are available, for example, from the General Electric Company as the Viscasil series and from Dow Corning as the Dow Corning 200 series. The polyalkylaryl siloxane fluids that may be used include, for example, those with viscosities of from about 0.65 to about 30,000 centistokes at 25° C. These siloxanes are available, for example, from the General Electric Company as SF 1075 methyl phenyl fluid or from Dow Corning as 556 Cosmetic Grade Fluid.

Also suitable for use are certain volatile cyclic polydimethylsiloxanes of the formula:

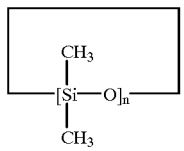

wherein "n" is equal to about 3 to about 7.

The viscosity can be measured by means of a glass capillary viscometer as set forth in Dow Corning Corporate Test Method CTM0004, Jul. 29, 1970. Preferably the viscosity ranges from about 350 centistokes to about 100,000 centistokes. A preferred silicone fluid useful herein is Dow Corning 344, marketed by the Dow Corning Corporation.

Emulsions:

Preferred compositions comprise an emulsion of the anhydrous silicone mixture in water. Preferably, in such compositions, the ethylene oxide/propylene oxide silicone copolymer is present at a level of from about 0.1% to about 10%, more preferably from about 0.1% to about 3%. Preferably, the ethylene oxide silicone copolymer is present at a level of from about 0.01% to about 10%, more preferably from about 0.05% to about 3%. Preferably, the silicone gum is present at a level of from about 0.1% to about 10%, more preferably from about 0.1% to about 3%. Preferably, the silicone fluid is present at a level of from about 0.1% to about 15%, more preferably from about 0.1% to about 5%. All percentages herein are by weight of total composition, unless indicated otherwise.

The compositions of this invention are made by adding the preblended mixture of anhydrous silicone mixture to water. The anhydrous silicone mixture is prepared by mixing together the various silicone ingredients until a uniform blend is obtained. Optional materials may be added to the mixture. The anhydrous silicone mixture is then added directly to the water. Optional materials may be added to the water prior to mixing. Preferably, the anhydrous silicone mixture contains (by weight of such mixture) from about 1% to about 35% of the ethylene oxide/propylene oxide silicone surfactant; from about 0.1% to about 10% of the ethylene oxide silicone surfactant; and from about 1% to about 65% the silicone gum. The anhydrous silicone mixture is preferably added to water at a level of from about 0.5% to about 10%.

Active Ingredients:

The compositions of this invention preferably contain a safe and effective amount of a cosmetic active, a pharmaceutical active, or mixtures thereof. Preferred active materials useful herein provide cosmetic and/or pharmocologic benefits for the prevention, treatment or amelioration of acne (herein referred to as "acne regulating agents"). Acne regulating agents include materials that modify the surface of the skin, inhibit sebum production, affect the physical properties of sebum, have an antibacterial activity on bacteria associated with acne, or otherwise prevent or treat acne. Acne regulating agents useful herein include, without limitation, antiinfectives, antiinflammatories, antiandrogens, keratolytic agents, and sebum controlling agents. Actives are preferably present at a level of from about 0.1% to about 12%, more preferably from about 0.5% to about 5%, more preferably from about 1% to about 3%.

Preferred active materials useful herein also include sebum controlling agents. "Sebum controlling agents," as referred to herein, include cosmetic or pharmaceutical active materials that reduce the perceived level of sebum on skin, improving the visual appearance, texture or feel of skin. Preferred sebum controlling agents useful herein include nicotinic acid, niacinamide, cucumber extract, panthenol, pantothenic acid, pyridoxine, riboflavin, retinoids, hesperitin, phloretin, and mixtures thereof Such agents may be included as substantially pure materials, or as extracts obtained by suitable physical and/or chemical isolation from natural (e.g., plant) sources. Cucumber extracts are commercially available from a variety of sources, including Active Organics, Grau, Alban Miller, Novarom, Dracgoco, Phytocim, and Cosmetochem. Preferred sebum controlling agents include niacinamide, cucumber extract, panthenol, and pyridoxine. A particularly preferred sebum controlling agent is niacinamide.

Antiinfectives useful herein include any naturally derived, synthetic, or semisynthetic antiinfectives with activity against P. acnes or other bacteria associated with acne. Preferred antiinfectives include without limitation, benzoyl peroxide, salicylic acid octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, erythromycin, clindamycin, and meclocycline. Benzoyl peroxide is a preferred antibacterial.

Antiinflammatories useful herein include corticosteroids such as hydrocortisone, cortisone, meprednisone, paramethasone, prednisolone, prednisone, beclomethasone, triamcinolone. Antiinflammatories also include nonsteroidal antiinflammatory agents such as ibuprofen, naproxen, flufenamic acid, mefenamic acid, meclofenamic acid, piroxicam and felbinac.

Keratolytic agents useful herein include salicylic acid (o-hydroxybenzoic acid), derivatives of salicylic acid such as 5-octanoyl salicylic acid, and resorcinol. Salicylic acid is a preferred keratolytic agent.

Retinoids useful herein include retinoic acid, and all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

Antiandrogens useful herein compounds capable of correcting androgen-related disorders by interfering with the action of androgens at the skin. Preferred antiandrogens include cyproterone thiopivalate and cyproterone acetate thioacetate.

The active ingredients useful herein are categorized by their cosmetic and/or therapeutic benefit or their postulated mode of action. However, it is to be understood that the active ingredients useful herein can in some instances provide more than one cosmetic and/or therapeutic benefit or operate via more than one mode of action. Therefore, classifications herein are made for the sake of convenience and are not intended to limit the active ingredient to that particular application or applications listed.

Water:

The compositions of the present invention comprise from about 45% to about 99.7%, preferably from about 60% to about 95%, more preferably from about 70% to about 90% of water. The exact level of water will depend upon the form of the product and the desired moisture content.

Optional Components:

The compositions of the present invention may contain a wide range of additional, optional components. The *CTFA Cosmetic Ingredient Handbook*, Second Edition, 1992, which is incorporated by reference herein in its entirety, describes a wide variety of cosmetic and pharmaceutical ingredients commonly used in skin care compositions, which are suitable for use in the compositions of the present invention. Nonlimiting examples of functional classes of ingredients are described at page 537 of this reference. Examples of these functional classes include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include, for example, emulsifiers, sequestrants, and skin sensates.

In particular, the compositions of this invention may contain an optional water-soluble humectant. A preferred humectant is glycerine (sometimes known as glycerol or glycerin) and derivatives thereof (e.g., propoxylated glycerine and ethoxylated glycerine). Other useful humectants include D-panthenol, hyaluronic acid, glucosides (e.g., Glucam E10 and E20 available from Amerchol Corporation), lactamide monoethanolamine, and acetamide monoethanolamine. When used in the present invention, the water-soluble humectant is preferably present at a level of from about 0.5% to about 20%, more preferably from about 1% to about 10%, and more preferably from about 4% to about 8%.

The compositions of the present invention may also contain an optional hydrophilic gelling agent at a level preferably from about 0.1% to about 20%, more preferably from about 0.2% to about 5%, and more preferably from about 0.3% to about 4%. The gelling agent preferably has a neutralized viscosity (1% aqueous solution, 20° C., Brookfield RVT) of at least about 500 cps, more preferably at least about 10,000 cps, and most preferably at least about 50,000. Suitable hydrophilic gelling agents include water-soluble or colloidally water-soluble polymers, and include cellulose ethers (e.g. hydroxyethyl cellulose, methyl cellulose, hydroxy propylmethyl cellulose), polyvinylpyrrolidone, polyvinylalcohol, guar gum, hydroxypropyl guar gum and xanthan gum. Hydrophilic gelling agents optionally useful herein also include carboxylic acid copolymers. These copolymers consist essentially of a colloidally water-soluble polymer of acrylic acid crosslinked with a polyalkenyl polyether of a polyhydric alcohol, and optionally an acrylate ester or a polyfunctional vinylidene monomer. Examples of carboxylic acid copolymers useful in the present invention include Carbomer 934, Carbomer 941, Carbomer 950, Carbomer 951, Carbomer 954, Carbomer 980, Carbomer 981, Carbomer 1342, acrylates/C10–30 alkyl acrylate cross polymer (available as Carbopol 934, Carbopol 941, Carbopol 950, Carbopol 951, Carbopol 954, Carbopol 980, Carbopol 981, Carbopol 1342, and the Pemulen series, respectively, from B.F. Goodrich). Other carboxylic acid copolymers useful in the present invention include sodium salts of acrylic acid/acrylamide copolymers sold by the Hoechst Celanese Corporation under the trademark of Hostaceren PN73, hydrogel polymers sold by Lipo Chemicals Inc. under the trademark of HYPAN hydrogels.

The compositions of this invention may contain surfactant materials. Such optional surfactant materials may be anionic, cationic, amphoteric, non-ionic, or mixtures thereof Surfactant materials useful herein are disclosed in the following documents, all of which are incorporated by reference herein: McCutcheon's, *Detergents and Emulsifiers*, North American edition (1986), published by Allured Publishing Corporation; McCutcheon's, *Functional Materials*, North American Edition (1992); and U.S. Pat. No. 3,929,678, Laughlin et al., issued Dec. 30, 1975.

Amphoteric surfactants useful herein include those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Preferred amphoteric or zwitterionic surfactants are the betaines, sultaines, and hydroxysultaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl di-methyl gamma-carboxypropyl betaine, lauryl bis-(2-hydroxypropyl)alpha-carboxyethyl betaine, coco dimethyl sulfopropyl betaine, stearyl dimethyl sulfopropyl betaine, stearyl betaine, lauryl dimethyl sulfoethyl betaine, lauryl bis-(2-hydroxyethyl) sulfopropyl betaine, and amidobetaines and amidosulfobetaines , oleyl betaine (available as amphoteric Velvetex OLB-50 from Henkel), and cocamidopropyl betaine (available as Velvetex BK-35 and BA-35 from Henkel). Examples of sultaines and hydroxysultaines include materials such as cocamidopropyl hydroxysultaine (available as Miataine CBS from Rhone-Poulenc).

Anionic surfactants amongst those useful herein include alkoyl isethionates, alkyl and alkyl ether sulfates, succinamates, olefin sulfonates having about 12 to about 24 carbon atoms, b-alkyloxy alkane sulfonates, sarcosinates, soaps (i.e. alkali metal salts, e.g., sodium or potassium salts) of fatty acids), and phosphates. Nonlimiting examples of alkoyl isethionates include ammonium cocoyl isethionate, sodium cocoyl isethionate, sodium lauroyl isethionate, sodium stearoyl isethionate, and mixtures thereof Nonlimiting examples of the succinamates are sodium lauryl sulfate and ammonium lauryl sulfate. A nonlimiting example of the sarcosinates is sodium lauroyl sarcosinate Nonlimiting examples of preferred anionic surfactants useful herein include those selected from the group consisting of sodium lauryl sulfate, ammonium lauryl sulfate, ammonium cetyl sulfate, sodium cetyl sulfate, sodium stearyl sulfate, ammonium cocoyl isethionate, sodium lauroyl isethionate, sodium lauroyl sarcosinate, and mixtures thereof A particularly preferred anionic surfactant useful herein is sodium lauryl sulfate.

Cationic surfactants optionally useful include cationic ammonium salts and amino-amides. Nonlimiting examples of cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof Nonlimiting examples of quaternary ammonium salt cationic surfactants include cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof Nonlimiting examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof Methods This invention also provides methods for regulating sebum on the skin of a human subject, comprising applying to said subject an emulsion composition comprising (a) an anhydrous silicone mixture comprising
 (i) an ethylene oxide/propylene oxide silicone copolymer;
 (ii) an ethylene oxide silicone copolymer;
 (iii) a silicone gum; and
 (iv) a volatile silicone fluid; and
(b) water.

Preferably, the composition additionally comprises a safe and effective amount of a cosmetic active, a pharmaceutical active, or mixtures thereof, as described above. Preferred methods of this invention comprise applying a composition containing a sebum controlling agent. As used herein, "regulating sebum" refers to reducing the actual and/or perceived level of oil on skin. Preferred methods of this invention comprise regulating sebum on facial skin.

The following non-limiting examples further describe and demonstrate the compositions and methods of this invention. The examples are given solely for the purpose of illustration and are not to be construed as limitations of the present invention, as many variations thereof are possible.

EXAMPLE 1

A composition according to this invention is made comprising the following materials.

| Component | % (by weight of total composition) |
| --- | --- |
| niacinamide | 2.00 |
| Dow Corning 344[a] | 1.22 |
| Dow Corning Q2-1401[b] | 0.58 |
| Dow Corning QZ-3225C[c] | 0.58 |
| Dow Corning 193[d] | 0.12 |
| glycerin | 2.08 |
| butylene glycol | 0.12 |
| Pemulen TR-1[e] | 0.25 |
| Carbopol 980[f] | 0.20 |
| Glydant Plus[g] | 0.20 |
| disodium EDTA | 0.10 |
| sodium hydroxide | 0.08 |
| water | 92.47 |

[a]silicone fluid, marketed by Dow Corning Corporation
[b]silicone gum (blend of dimethiconol and cyclomethicone), marketed by Dow Corning Corporation
[c]ethylene oxide/propylene oxide silicone copolymer (blended with cyclomethicone), marketed by Dow Corning Corporation
[d]ethylene oxide silicone copolymer, marketed by Dow Corning Corporation
[e]carboxylic acid copolymer, marketed by B. F. Goodrich Company
[f]carboxylic acid copolymer, marketed by B. F. Goodrich Company
[g]preservative, marketed by Lonza Corporation The composition is made by first slowly adding the Carbopol and Pemulen to water. The mixture is stirred for approximately one hour at approximately 55° C. is The mixture is then cooled to approximately 33° C. The EDTA, niacinamide and glycerin are then added to the water mixture.

The butylene glycol and Glydant are mixed until the Glydant is dissolved. This mixture is then added to the water. Sodium hydroxide is then added to the water, and mixed for approximately 17 minutes.

The silicone materials are then mixed, using a prop mixer. This mixture is then added to the water mixture and the resulting composition mixed for approximately 40 minutes.

Compositions are made according to this example, replacing niaciniamide with D-panthenol, cucumber extract, nicotinic acid, pantothenic acid, pyrioxine, riboflavin, hesperitin, and phloretin, with substantially similar results.

The resulting composition is applied to the skin of a human subject suffering from excess sebum production. Following application, the skin is observed, visually and by feel, to have significantly decreased oiliness.

EXAMPLE 2

A composition according to this invention is made comprising the following materials.

| Component | % (by weight of total composition) |
|---|---|
| cucumber extract | 2.00 |
| Vitamin E acetate | 1.00 |
| Dow Corning 344 | 1.22 |
| Dow Corning Q2-140L | 0.58 |
| Dow Corning QZ-3225C | 0.58 |
| Dow Corning 193 | 0.12 |
| glycerin | 4.00 |
| stearyl alcohol | 2.25 |
| cetyl alcohol | 2.25 |
| glycerol hydroxy stearate | 0.74 |
| Brij 700[a] | 0.50 |
| butylene glycol | 1.00 |
| Glydant Plus | 0.20 |
| Stabileze[b] | 1.00 |
| disodium EDTA | 0.10 |
| fragrance | 0.01 |
| water | 82.45 |

[a]emulsifier, manufactured by ICI Americas
[b]thickener, manufactured by GAF-ISP The stearyl alcohol, cetyl alcohol, glycerol hydroxy stearate, Brij 700, and fragrance are mixed to form an oil phase mixture. The cucumber extract, Glydant Plus, butylene glycol, Stabilize, EDTA are mixed with water. The oil phase mixture and water mixture are then mixed at approximately 65° C., and homogenized for approximately 5 minutes. The mixture is cooled to approximately 35° C. Separately, the silicones are mixed with glycerin and Vitamin E acetate. This mixture is then added to the water/oil phase mixture.

The resulting composition is applied to the face of a human subject, daily, for three months. Following application, the skin is observed, visually and by feel, to have significantly decreased oiliness.

EXAMPLE 3

A composition according to this invention is made comprising the following materials.

| Component | % (by weight of total composition) |
|---|---|
| salicylic acid | 1.00 |
| hesperetin | 1.00 |
| menthol | 0.10 |
| Vitamin E acetate | 1.00 |
| glycerin | 4.00 |
| Dow Corning 344 | 1.22 |
| Dow Corning Q2-1401 | 0.58 |
| Dow Corning QZ-3225C | 0.58 |
| Dow Corning 193 | 0.12 |
| PEG 30 | 1.00 |
| Sepigel 305* | 3.00 |
| disodium EDTA | 0.10 |
| ethanol | 30.00 |
| water | 56.30 |

*thickener, manufactured by Seppic

The ethanol, salicylic acid, PEG 30, EDTA, menthol, hesperetin, Sepigel and water are mixed. Separately the silicones are mixed with the glycerin and Vitamin E acetate. The silicone mixture is then added to the water mixture, and homogenized for approximately 5 minutes.

The resulting composition is applied to the face of a human subject having acne. Following application, the skin is observed to have significantly decreased oiliness, and the number of acne lesions is reduced after a period of six months of daily use.

What is claimed is:
1. A method for the treatment of acne on the skin of a human subject comprising applying to said skin a skin care emulsion composition comprising:
(a) from about 0.1% to about 12% of an acne regulating agent selected from the group consisting of antiinfectives, nicotinic acid, niacinamide, cucumber extract, panthenol, pantothenic acid, pyridoxine, riboflavin, hesperitin, phloretin, retinoids, antiinflammatories, keratolytic agents, antiandrogens, and mixtures thereof;
(b) an anhydrous silicone mixture comprising
(i) from about 0.1% to about 10% of an ethylene oxide/propylene oxide silicone copolymer of the formula

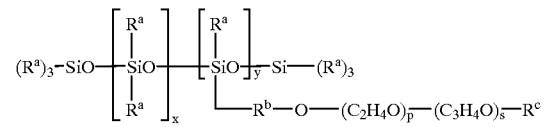

wherein $R^a$ is an alkyl group of one to six carbon atoms; $R^b$ is the radical $-C_mH_{2m}-$; $R^c$ is a terminating radical which is hydrogen, an alkyl group of one to six carbon atoms, or phenyl; "mm" has a value of two to eight; "p" and "s" have values such that the oxyalkylene segment $-(C_2H_4O)_p-(C_3H_6O)_s-$ has a molecular weight in the range of 400 to 5,000; "x" has a value of 80 to 120; and "y" has a value of 2 to 10;
(ii) from about 0.01% to about 10% of an ethylene oxide silicone copolymer of the formula

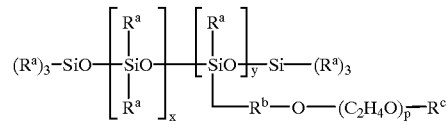

wherein $R^a$ is an alkyl group of one to six carbon atoms; $R^b$ is the radical $-C_mH_{2m}-$; $R^c$ is a terminating radical is hydrogen, an alkyl group of one to six carbon atoms, or phenyl; "m" has a value of two to eight; "p" has a value of 8 to 16; "x" has a value of 6 to 12; and "y" has a value of 1 to 8;
(iii) from about 0.1% to about 10% of a silicone gum; and
(iv) from about 0.1% to about 15% of a silicone fluid; and
(c) water.
2. A method according to claim 1, wherein said acne regulating agent is selected from the group consisting of niacinamide, panthenol, pyridoxine, pantothenic acid, cucumber extract, retinoids, salicylic acid and mixtures thereof.
3. A method according to claim 2, wherein said acne regulating agent is selected from the group consisting of niacinamide, retinoids, salicylic acid and mixtures thereof.
4. A method according to claim 2, wherein said acne regulating agent is niacinamide.
5. A method according to claim 2, wherein said acne regulating agent is salicylic acid.
6. A method for the treatment of acne on the skin of a human subject comprising applying to said skin a skin care emulsion composition comprising:

(a) from about 0.1% to about 12% of a sebum controlling agent selected from the group consisting of nicotinic acid, niacinamide, cucumber extract, panthenol, pantothenic acid, pyridoxine, riboflavin, retinoids, hesperitin, phloretin, and mixtures thereof;

(b) an anhydrous silicone mixture comprising (i) from about 0.1% to about 10% of an ethylene oxide/propylene oxide silicone copolymer of the formula

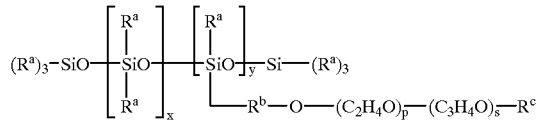

wherein $R^a$ is an alkyl group of one to six carbon atoms; $R^b$ is the radical $-C_mH_{2m}-$; $R^c$ is a terminating radical which is hydrogen, an alkyl group of one to six carbon atoms, or phenyl; "m" has a value of two to eight; "p" and "s" have values such that the oxyalkylene segment $-(C_2H_4O)_p-(C_3H_6O)_s-$ has a molecular weight in the range of 400 to 5,000; "x" has a value of 80 to 120; and "y" has a value of 2 to 10;

(ii) from about 0.01% to about 10% of an ethylene oxide silicone copolymer of the formula

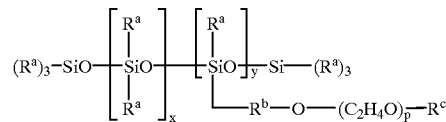

wherein $R^a$ is an alkyl group of one to six carbon atoms; $R^b$ is the radical $-C_mH_{2m}-$; $R^c$ is a terminating radical is hydrogen, an alkyl group of one to six carbon atoms, or phenyl; "m" has a value of two to eight; "p" has a value of 8 to 16; "x" has a value of 6 to 12; and "y" has a value of 1 to 8;

(iii) from about 0.1% to about 10% of a silicone gum; and (iv) from about 0% to about 15% of a volatile silicone fluid; and (c) water.

7. A method according to claim 6, additionally comprising a humectant.

8. A method according to claim 7, wherein said humectant is glycerin.

9. A method according to claim 6, additionally comprising a surfactant material.

10. A method according to claim 6, wherein said sebum controlling agent is niacinamide.

11. A method according to claim 7, additionally comprising an antiinfective agent.

12. A method according to claim 6, additionally comprising salicylic acid.

* * * * *